(12) United States Patent
Mazyck et al.

(10) Patent No.: US 8,980,171 B2
(45) Date of Patent: Mar. 17, 2015

(54) SYSTEM AND METHOD FOR PURIFYING AIR VIA LOW-ENERGY, IN-SITU REGENERATED SILICA-TITANIA COMPOSITES

(76) Inventors: David W. Mazyck, Gainesville, FL (US); Anna I. Casasus, Norcross, GA (US)

( * ) Notice: Subject to any disclaimer, the term of this patent is extended or adjusted under 35 U.S.C. 154(b) by 597 days.

(21) Appl. No.: 12/903,543

(22) Filed: Oct. 13, 2010

(65) Prior Publication Data
US 2011/0085933 A1   Apr. 14, 2011

Related U.S. Application Data

(60) Provisional application No. 61/251,164, filed on Oct. 13, 2009.

(51) Int. Cl.
*A61L 9/00* (2006.01)
*A61L 9/20* (2006.01)

(52) U.S. Cl.
CPC ............ *A61L 9/205* (2013.01); *A61L 2202/25* (2013.01)
USPC .............................................. 422/4; 422/122

(58) Field of Classification Search
USPC .................................................... 422/4, 122
See application file for complete search history.

(56) References Cited

U.S. PATENT DOCUMENTS

| | | | |
|---|---|---|---|
| 6,358,374 B1* | 3/2002 | Obee et al. | 204/157.3 |
| 2002/0050450 A1* | 5/2002 | Newman et al. | 204/157.3 |
| 2006/0067854 A1* | 3/2006 | Andino et al. | 422/22 |

* cited by examiner

*Primary Examiner* — Kevin Joyner
(74) *Attorney, Agent, or Firm* — Squire Patton Boggs (US) LLP

(57) ABSTRACT

A system and method for purifying air via low-energy, in-situ regenerated silica-titania composites is described. The silica-titania composites can be synthesized with various pore sizes, photocatalyst loadings, and surface area, and can be applied in pellet/granular form or powdered and coated onto a surface. The system may operate with continuous UV irradiation for continuous oxidation of pollutants and inactivation of pathogens. Alternatively, the system may operate with intermittent UV irradiation, whereby pollutants are adsorbed in the absence of light, followed by oxidation of sorbed pollutants and regeneration of silica-titania composites upon irradiation with UV light. The oxidation/regeneration step may or may not incorporate sweep air. This system and method may be used for removing pollutants, such as Volatile Organic Compounds, from aircraft cabins, space exploration vehicles and architectures, mass transit vehicles, and residential and commercial buildings.

3 Claims, 4 Drawing Sheets

SYSTEM AND METHOD FOR PURIFYING AIR VIA LOW-ENERGY, IN-SITU REGENERATED SILICA-TITANIA COMPOSITES

PRIORITY APPLICATION

This application claims the benefit of the priority under 35 USC §§119 and 120 of U.S. Provisional Application No. 61/251,164 filed Oct. 13, 2009, the entire disclosure of which is hereby incorporated by reference.

STATEMENT REGARDING FEDERALLY SPONSORED RESEARCH OR DEVELOPMENT

The U.S. Government has certain rights to the invention based on Environmental Protection Agency Grant/Contract No. EP-D-09-034 with Sol-gel Solutions, LLC.

BACKGROUND

Without limiting the scope of the invention, its background will be described in relation to a system and method for purifying air via low-energy, in-situ regenerated silica-titania composites, as an example.

"Sick building syndrome," used to describe acute negative health effects linked to time spent in a building, has been related to poor indoor air quality. Similarly, poor aircraft cabin air quality has been identified as a cause for negative health effects on pilots and flight crews, leading to numerous studies on "aerotoxic syndrome." Symptoms of aerotoxic syndrome include headache, eye and nose irritation, cough, shortness of breath, chest tightness, increased heart rate, light-headedness, dizziness, blurred or tunnel vision, disorientation, confusion, memory impairment, shaking and tremors, loss of balance, vertigo, nausea, vomiting, seizures, and loss of consciousness. These symptoms can pose a serious threat if experienced by pilots and/or crew during flight.

Volatile organic compounds ("VOCs") are a major source of indoor air pollution in aircraft and buildings. Sources of indoor VOCs include cleaners, building materials, furniture, human bioeffluents, cosmetics, food, and beverages, among others. In the case of aircraft cabins, ethanol is usually the VOC present at the highest concentrations.

In addition to the VOCs present in aircraft cabins due to off gassing from surfaces and human activities, the occurrence of "fume events" results in the release of more toxic gases, such as tricresyl phosphate, into aircraft cabins. Because engines have a source of compressed air for fuel combustion, this is a convenient source for providing compressed air to the cabin. Thus, air is bled from the engines upstream of the combustion chamber to supply the cabin air conditioning system. This bleed air, which is not filtered, may become contaminated with hydraulic oils prior to reaching the cabin. This leakage of hydraulic oil gases into the cabin is referred to as a fume event, and has been linked to the more severe symptoms of aerotoxic syndrome.

Technologies that can safely, economically, and effectively degrade VOCs from indoor air are necessary to protect human health. The most commonly used technology at present is activated carbon filters, which, although effective initially, quickly become saturated and must be disposed of and replaced. Additionally, carbon filters simply adsorb VOCs, rather than destroy them.

While the use of UV alone (i.e., photolysis) has been considered for this type of application, it may result in production of potentially hazardous oxidation intermediates if a photocatalyst is not present. Thin films of photocatalysts (e.g., titanium dioxide, also known as $TiO_2$ or titania) on metal panels or other surfaces are a plausible option, but have a much lower surface area than the silica-titania composites described herein, and thus result in less effective oxidation. A combination of activated carbon, titania, and UV may also be used, but will also be less effective.

Ozonation has been considered, but excess ozone may be hazardous to human health. Other options include catalytic oxidation, which requires temperatures above 150° C. and may be poisoned by a fume event, and plasma oxidation, which results in generation of ozone and has critical residence time requirements to avoid production of oxidation intermediates.

SUMMARY

The above-described problems are solved and a technical advance is achieved by the system and method for purifying air via low-energy, in-situ regenerated silica-titania composites disclosed in this application.

The present system and method include purification and revitalization of air in residential and commercial buildings, aircraft, and space exploration vehicles and architectures. More particularly, the invention relates to removal of volatile organic compounds ("VOCs") from a fluid stream by adsorption and either subsequent or continuous catalytic and photocatalytic oxidation using catalyst- and photocatalyst-impregnated or doped sorbents (e.g., synthesized silica gels) for destruction of the VOCs and regeneration of the silica gels. More specifically, this invention relates to the adsorption of VOCs onto the synthesized photocatalyst-impregnated silica gels, followed by ultraviolet ("UV") irradiation of said material such that the original adsorption capacity is restored. The system will also remove inorganic compounds and inactivate pathogens.

To overcome some of the deficiencies of typical photocatalytic systems, the present system and method includes a novel, porous, high surface area silica-gel adsorbent impregnated with titania; herein referred to as Silica-Titania Composites ("STC"). The STC are normally employed as a packed bed of pellets, and irradiated with UV light, promoting simultaneous adsorption and oxidation (see United States Publication No. 2006/0096926).

In the context of VOCs, oxidation in closed environments raises concerns about release of oxidation intermediates. Because the STC have high adsorption capacity for several contaminants, continuous irradiation is not necessary for pollutant removal. Thus, the present system and method include adsorbing VOCs during flight (without UV), with regeneration (UV irradiation for destruction of sorbed VOCs) on the tarmac, after passengers disembark, while the aircraft is prepared for its next voyage. A small volume of recirculated sweep air may assist with regeneration, followed by exhausting to the atmosphere. In this manner, passengers and flight crews would be protected during flight, and if problematic intermediates are developed during regeneration, they can be vented to the atmosphere or to an on-the-tarmac adsorbent bed. Complete "mineralization" of adsorbed VOCs to water and carbon dioxide during regeneration is the desired goal, to avoid any venting of VOCs. The preferred method would be applicable to long-haul flights averaging 20 hours in duration, with preferably an at least 2-hour regeneration period, as well as for short (2 hours) or medium duration flights (4-6 hours) with a 30-minute to one-hour regeneration, for example.

Embodiments of the present invention may provide for the destruction of VOCs (i.e., oxidation of organic compounds to carbon dioxide and water) when irradiating with UV light, which results in the regeneration of the STC for reuse. Embodiments of the present invention may allow for reuse of the STC by UV irradiation in-situ.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

For a more complete understanding of the features and advantages of the system and method for purifying air via low-energy, in-situ regenerated silica-titania composites, reference is now made to the detailed description of the invention along with the accompanying figures in which corresponding numerals in the different figures refer to corresponding parts and in which.

DETAILED DESCRIPTION OF THE DRAWINGS

The term "exemplary" is used herein to mean "serving as an example, instance, or illustration." Any embodiment, aspect, or design described herein as "exemplary" is not necessarily to be construed as preferred or advantageous over other embodiments, aspects, or designs.

As used herein, the term "VOCs" refers to a variety of volatile organic compounds. As used herein, the term "impregnated" refers to the incorporation of a material (e.g., a photocatalyst) within the porous network of a sorbent, and may be either attached to the surface of the pores and/or a part of the crystalline network. Also, as used herein, the term "doping" refers to the addition of a material such that it is fixed to the sorbent internal or external surface and is accessible to the fluid stream. Further, as used herein, the term "sorbent" refers to an amorphous or crystalline solid that is capable of accumulating contaminants on or within its porous network.

The present system and method are generally described below relative to an indoor or enclosed environment, such as an aircraft cabin. Nevertheless, the present system and method is applicable in any types of enclosed environments, such as buildings, vehicles, and the like. In certain embodiments, a method may purify air in aircraft cabins. The method may include adsorbing, during intermittent periods, volatile organic compounds with silica-titania composites in the absence of UV light during flights, when passengers and crew are present. The method may also include irradiating the silica-titania composites with one or more UV light sources of peak wavelengths below 400 nm on the tarmac, when passengers and crew have disembarked, for oxidation of sorbed compounds.

Figure 1:
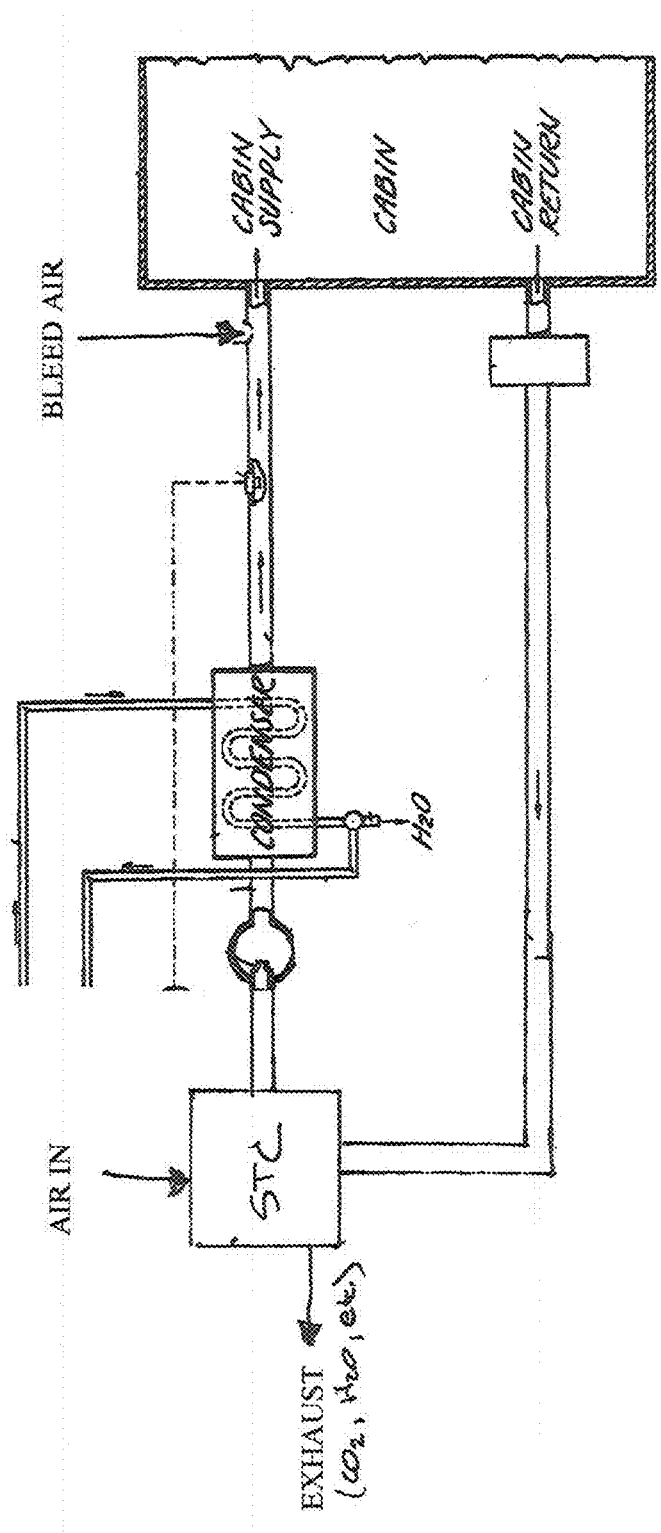
FIG. 1 is an illustration of an exemplary aircraft cabin including a system for purifying air via low-energy, in-situ regenerated silica-titania composites according to one embodiment.

FIG. 1 is an illustration of a cabin of an aircraft having a cabin supply of air and a cabin return of air in communication with a STC system. The cabin return may provide gas to the STC system. Air may enter the STC system from outside the STC system. Exhaust, such as $CO_2$, $H_2O$, etc., may exit the STC system. Additionally, the cabin may be serviced by a condenser for removing humidity or precipitation from the air entering the cabin. The processed air from the STC system may pass through the condenser prior to returning to the cabin. Also, the cabin may be serviced by bleed air provided from a source on the aircraft, such as an engine.

Figure 2:
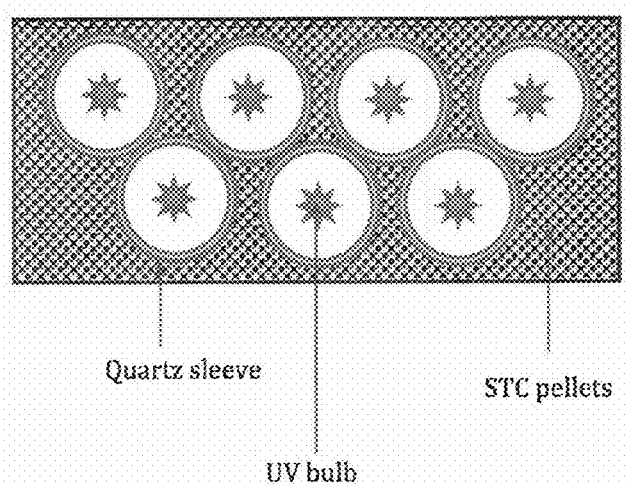
FIG. 2 is an illustration of a cross-section view of the STC bed according to one embodiment.

Referring now to FIG. 2, an illustration of an exemplary STC system is shown. Quartz or other similar materials may form sleeves encasing UV light sources, such as bulbs, lamps, LEDs, etc. Compression fittings may hold quartz sleeves. An STC bed may surround the quartz sleeves. A porous plate may also be present. As shown in FIG. 2, the quartz sleeves may surround the UV light sources, and the STC pellets may surround the quartz sleeves.

The present system and method is targeted to remove VOCs via adsorption and subsequent oxidation (regeneration). Adsorption on the composite material allows VOCs to be concentrated while exposure to radiation of a given wavelength range ensures the oxidation of the adsorbate(s). Intermittent irradiation is preferred for the invention, which minimizes energy consumption of the process, and eliminates the risk of release of oxidation intermediates during certain applications, such as aircraft cabin air purification. High efficiency, large capacity, low energy, and regenerability are advantageous features of the system and method.

The porous composite material preferably consists of a high surface area substrate material; for example, a silica-gel impregnated with photocatalyst particles, such as $TiO_2$; herein referred as a "silica-titania composite" (STC, $SiO_2$—$TiO_2$ composite gel). The STC can provide a surface area of about a few $m^2/g$ to 1500 $m^2/g$. The gel is preferably a xerogel, defined as a gel that is obtained by evaporation of the liquid component at ambient pressure and temperatures below the critical temperature of the liquid. However, other gel forms may be used with the invention. Other suitable substrates include activated carbon, ceramics, metal silicates, alumina, zeolites, and the like, as well as nonporous substrates such as silica/glass beads, stainless steel, and the like.

The capacity of the porous composite material can be further increased by optimizing mass transfer of contaminants from the bulk fluid phase to the adsorption sites. For example, one could manipulate the gels' pore size distribution or decrease the particle size from the current 3 mm by 1 mm size tested herein. In the preferred embodiment, a pore size of about 30 Å has been shown to give optimum performance. More efficient regeneration may be obtained by incorporating recirculated or vented sweep air during irradiation periods to minimize concentration gradients within the packed bed and to increase the availability of oxygen for redox reactions to take place. This sweep air may be ambient temperature to 120° C. In other embodiments, no room temperature to 120° C. sweep air is incorporated. Alternatively to UV irradiation, thermal regeneration (to temperatures up to 450° C.) of the composite is viable.

Photocatalyst particle (e.g., $TiO_2$) loading at all levels has been found to enhance oxidation. Optimal loading is a function of sorbent porosity, surface area, transparency to desired light wavelengths, permeability, adsorption characteristics, granular size, and other physical and chemical characteristics. In the preferred embodiment, a $TiO_2$ loading between 4 and 13 wt. % has been shown to give optimum performance.

In the preferred embodiment, the STC gel is formed using a sol-gel method. However, other methods to form the composite will be apparent to those skilled in the art. The basic formula uses specific volumetric ratios of various acids, water, silica alkoxide (silica precursor) or sodium silicate, with or without, various co-solvents. During formulation, during gelation, or post-gelation, the silica is doped, for example, with a commercially available photocatalyst, such as titanium dioxide. Preferably, the titania percentage varies from about 0.5% to about 32% on a wt/wt basis, but $TiO_2$ loadings up to 100 wt. % can be incorporated. Mixed alkoxide synthesis can also be used to form the STC with a more homogeneous distribution of titania. Various synthesis and aging steps can produce composites with pore sizes ranging from <10 angstrom to >50 nm or as large as desired. Preferably, the pore sizes are greater than about 30 angstroms and less than about 320 angstroms. In addition, surface treatments can be used to enhance adsorption. When the solution becomes viscous during a gelation step, it may be transferred into a mold to create a pellet of a desired size. After gelation, the composite may be aged for varying lengths of time to increase its strength. After aging, the pellets may be removed from their mold and placed in another container for additional heat treatment. In the preferred embodiment, the pellets are placed in an oven and the temperature may be ramped from room temperature to 103° C. and kept constant for 18 hours, resulting in vaporization of the liquid solvents within the porous silica matrix to form a xerogel. The temperature may then be ramped to 180° C. and kept constant for six hours. Additional curing at higher temperatures can be achieved (up to 600° C.) to strengthen the gel. The resultant average pore size of the gel can range from 30 angstrom to about 320 angstrom, depending on the initial formula. The pellets can then be used in a packed column.

This indicated only one exemplary composite formulation. A wide variety of formulations, catalysts, aging, and drying parameters can be used to derive the optimum pore size, pellet/particle size, surface area, surface adsorption characteristics, reduction efficiency, permeability, temperature stability, and regeneration characteristics. Alternatively, the sorbent can be synthesized in bulk and crushed or ground and screened to produce granular particles of the optimum size range for various applications. Crushed/ground sorbent can be incorporated in a number of solvents and used for coating a surface, such as a porous fabric.

A significant difference between the composites described herein and other composites for pollutant removal is the use of a UV-transparent substrate material, such as silica. Porous silica is a good adsorbent medium that is also substantially optically transparent to UV light, which allows the penetration of UV light through its matrix to activate the intermixed photocatalyst particles, such as titanium dioxide. Preferably, the photocatalyst particles are provided both on the surface and within the silica matrix allowing oxidation to occur on both external and internal surfaces within the porous silica structure.

A wide variety of photocatalysts can be used with the invention. The sol-gel process is not limited to the use of titanium dioxide, but other catalysts such as $HgO$, $ZnO$, $V_2O$, $SnO_2$, or even modified $TiO_2$ catalysts coated with platinum or other conductive materials can also be used. In addition, the composites can be made into any shape convenient for use, such as spheres, cylinders, and others.

The present invention is further illustrated by the following examples, which include demonstrations of the superior performance of the advanced porous composite material for VOC removal. The examples are provided for illustration only and are not to be construed as limiting the scope or content of the invention in any way.

The bench-scale studies shown below relative to FIGS. 3-5 were determined by the following laboratory instruments and apparatuses. A source of compressed air was used for dilution of VOCs to desired inlet concentration. A source of specialty gas mix consisting of specific concentration of target VOC in air (e.g., 100 ppm$_v$, 1000 ppm$_v$) was also provided. A rotameter was used to control the flow of dilution air (e.g., 3 to 8 L/min) to feed an annular reactor having UV bulbs disposed therein. A mass flow controller was used to control the flow of the target VOC to achieve the desired inlet concentration when combined with dilution air. Samples from the inlet and outlet of the reactor were collected either on compound-specific fibers for GC/MS analyses or in chilled water impingers for GC/FID analyses. The UV bulbs were 12-inch long low-pressure mercury lamps (8-14 W, 254 or 365 nm) and they were used for regeneration of the STC. 1 mm by 3 mm synthesized photocatalyst-impregnated silica-gels were used to make these determinations.

Synthesis of Silica-Titania Composites

The silica-titania composites were made by a sol-gel method using nitric acid and hydrofluoric acid as catalysts to increase the hydrolysis and condensation rates, thereby decreasing the gelation time. The basic formula used to create gels with a pore size of roughly 30 angstrom is as follows: 50 mL water, 100 mL ethanol, 70 mL TEOS (tetraethylorthosilicate), 8 mL nitric acid (1N), and 2 mL HF (3%). Of course, one of ordinary skill in the art will recognize that silicon alkoxides, sodium silicate, colloidal silicas, slip casting or traditional ceramic techniques are suitable for use with the invention.

The chemicals were reagent grade and were added individually, in no particular order, to a polymethylpentene container. During this time, a known mass of Degussa (Dusseldorf, Germany) P25 $TiO_2$ was added to the batch and the percentage of titania recorded is given as a percent by weight of silica. A magnetic stir plate provided sufficient mixing, but care should be used to ensure that the $TiO_2$ is well dispersed in the sol and that the homogeneous distribution of $TiO_2$ is maintained throughout the gelation process. The solution (including the P25) was pipeted into polystyrene 384-well assay plates before complete gelation. After gelation, the plates were covered with lids and wrapped in foil to prevent premature evaporation. Next, the sample was aged at room temperature for two days, then at 65° C. for two days.

After aging, the pellets were removed from the container and placed in a Teflon container for the next series of heat treatments. A small hole in the lid of the container allowed slow and uniform drying of the gel. The pellets were then placed in an oven and the temperature was ramped from room temperature to 103° C. (2 degrees per min) and kept constant for 18 hours, resulting in the vaporization of liquid solution within the silica network. Next, the temperature was ramped to 180° C. (2 degrees per min) for removal of physically adsorbed water and hardening of the gel, where it was kept constant for 6 hours and then was slowly decreased back to room temperature over a 90 minute period. The resultant size of an individual cylindrical pellet after drying was approximately 3 mm in length with a diameter of 1 mm.

VOC Removal Methodology

Silica-Titania Composites formed using the synthesis method described above were tested in a packed bed reactor system to characterize the mechanisms and efficiency for VOC removal. The reactor system is described above. The flowrate of ethanol-laden air was 3 liters/min with a residence time in the reactor of 0.1 to 0.2 seconds. The initial ethanol concentration for experiments ranged from 1 to 3 ppm$_v$ and was controlled via adjustment of mass flow controllers and rotameters to control the ratio of dilution air to 1000 ppm$_v$ ethanol. Influent and effluent ethanol samples were collected via NCASI (1998) Chilled Impinger Method and analyzed via GC/FID. A stainless steel mesh (64 um opening) was used to hold the pellets inside the annular reactor. A 254 nm UV lamp (14-W) was placed at the center of the packed-bed reactor, and the pellets were randomly packed around the lamp. Between 5 and 10 mL of pellets were used in the experiments.

Figure 3:
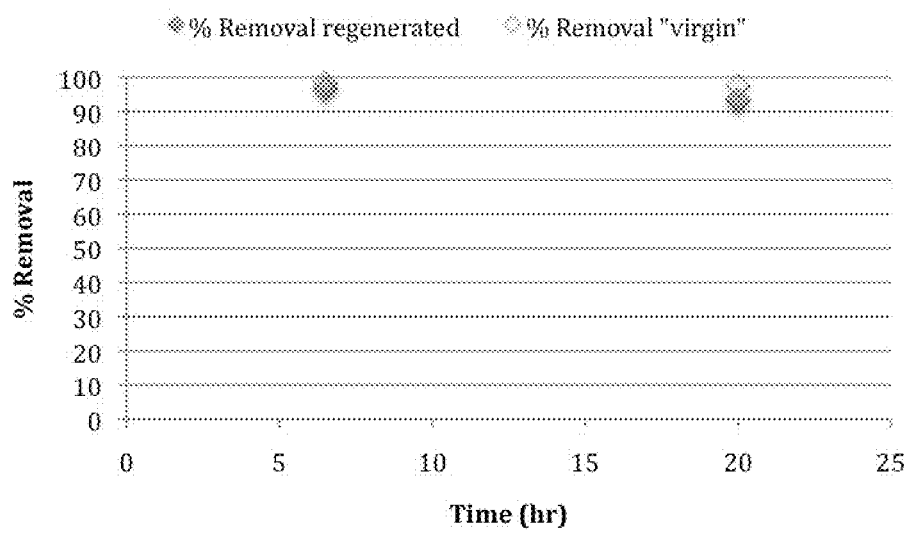
FIG. 3 is an illustration of a graph showing removal of ethanol with an exemplary STC according to one embodiment.

For intermittent UV studies, such as that presented in FIG. 3, the UV lamp was initially off. Ethanol-laden air was passed through the reactor for 20 hours, after which the flow to the reactor was stopped, inlet and outlet valves were closed, and the UV light was illuminated for 30 minutes to 2 hours. The UV lamp was then turned off and flow of ethanol to the reactor resumed for a 20-hour post-regeneration adsorption phase.

Flow rate is an important operating parameter that generally determines the VOC removal efficiency in the system. The flow rate controls the residence time of the ethanol-laden gas in the reactor, and therefore the effectiveness of adsorption can be impacted. Ethanol removal efficiency via adsorption as a function of residence time is shown in FIG. 5. As the residence time increased from 0.1 to 0.2 s there was significant improvement for the 20-hour data point. There was no significant difference in performance as the residence time was further increased to 0.5 s. The results of these determinations are shown and described below relative to FIGS. 3-5.

Referring now to FIG. 3, a graph illustrates the performance of an exemplary STC for the removal of 2 ppm$_v$ ethanol in air using intermittent irradiation (254 nm), with a 0.1 second residence time, and 15% relative humidity. A 20-hour adsorption phase (no irradiation) is followed by 2-hour regeneration (254-nm irradiation), which is followed by a post-regeneration adsorption phase. A 20-hour period is generally considered the longest flight time for which the invention may need to operate prior to passenger disembarkment and in-between-flight regeneration.

Figure 4:
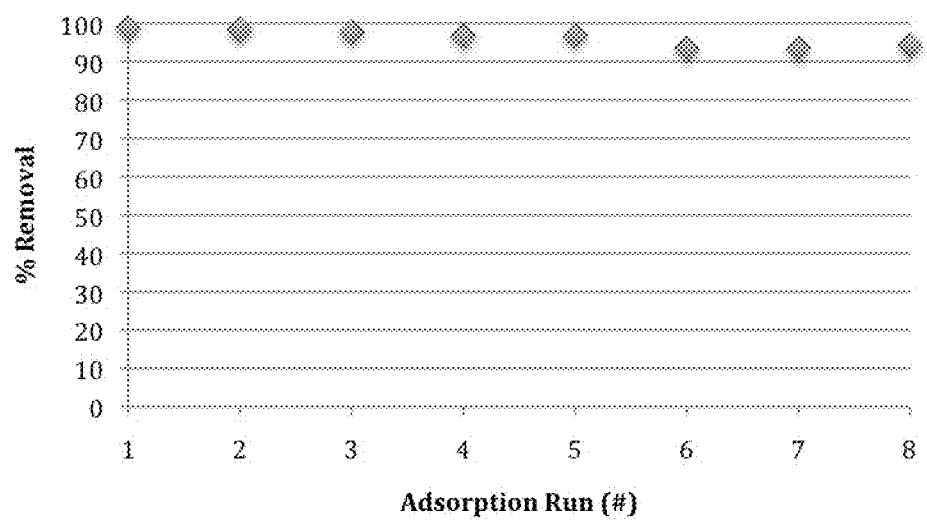
FIG. 4 is an illustration of a graph showing multiple 2-hour adsorption cycles with 30-minute regeneration cycles of an exemplary STC according to one embodiment.

Referring now to FIG. 4, a graph illustrates multiple cycles of adsorption followed by regeneration (254-nm irradiation). A concentration of 0.34 ppm$_v$ of toluene, a more challenging VOC, was used, with each adsorption cycle lasting two hours and each regeneration cycle lasting 30 minutes, plus a final regeneration period lasting four hours.

Figure 5:
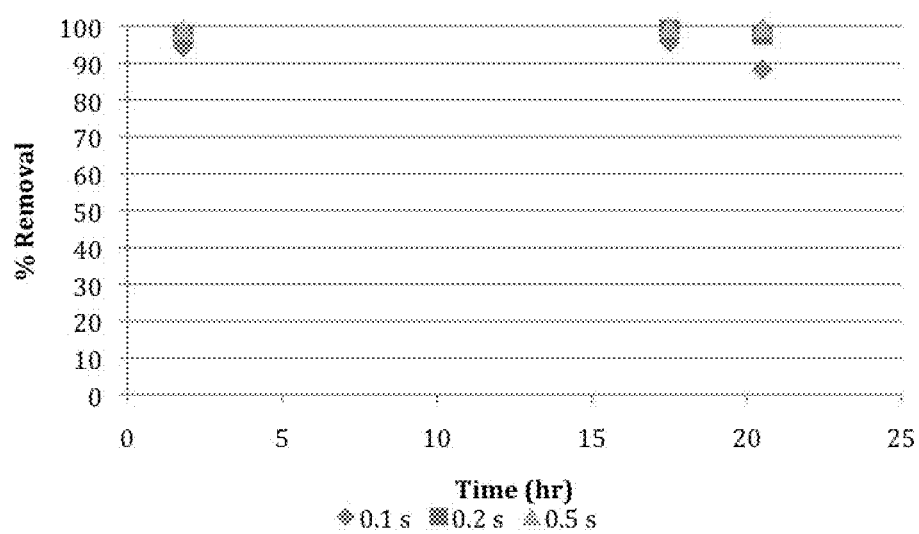
FIG. 5 is an illustration of a graph showing the effects of contact time on ethanol removal via adsorption with an exemplary STC according to one embodiment.

Referring now to FIG. 5, a graph illustrates the effect of contact time on ethanol removal via adsorption. An influent ethanol concentration of 2 ppm$_v$ was fed to a testing annular reactor, as described above. The volume of STC pellets was varied to obtain three different contact times at a constant flow rate (3 L/min).

In accordance with the present system and method, there is provided a method and composite for removing VOCs from a fluid stream, the method including the steps of contacting a composite material comprising a substrate and catalyst particles with a fluid stream. The composite material adsorbs and oxidizes VOCs in fluids. Preferably, the catalyst particles are located on the substrate surface and/or contained in the substrate. The composite material may be a sorbent and, if so, is preferably a gel, more preferably, a xerogel.

An exemplary method preferably includes the step of irradiating the composite material, preferably with radiation having a wavelength of from about 160 to about 680 nm. The substrate is preferably transparent to radiation and, for example, may be porous silica, and the catalyst may comprise TiO$_2$. The radiation source may be traditional mercury lamps, UV light emitting diodes ("UV LEDs"), or any source capable of providing light between the preferred wavelengths. Preferably, the sorbent is a material having a surface area (BET) of about 1 to about 1500 m$^2$/g, preferably about 200 to about 900 m$^2$/g. The catalyst is preferably present in an amount of from 0.1 wt % to about 100 wt %.

An exemplary method refers to intermittent irradiation of a packed bed of composite, thereby promoting the adsorption and subsequent oxidation of VOCs and regeneration of the composite for reuse. Intermittent irradiation is preferred for aircraft cabin air purification, where concerns of release of oxidation intermediates are apparent.

In addition to the aforementioned aspects and embodiments of the present system for making pellets, granules, and coatings, the present invention further includes methods for purifying air from an enclosed environment.

The previous detailed description is of a small number of embodiments for implementing the system and method for purifying air via low-energy, in-situ regenerated silica-titania composites and is not intended to be limiting in scope. One of skill in this art will immediately envisage the methods and variations used to implement this invention in other areas than those described in detail.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed:

1. A method for purifying air in aircraft cabins, the method comprising:
    adsorbing, during intermittent periods, volatile organic compounds with silica-titania composites in the absence of UV light during flights, when passengers and crew are present, wherein the silica-titania composites have pore sizes between about 30 and about 320 Angstroms, the silica-titania composites have photocatalyst concentrations between 4 wt % and 32 wt %, and the silica-titania composites are pellets or granules in a packed bed;
    irradiating the silica-titania composites in situ with one or more UV light sources of peak wavelengths below 400 nm on the tarmac, when passengers and crew have disembarked, for oxidation of sorbed compounds and regeneration of silica-titania composites for reuse;
    adding room temperature to 120° C. sweep air during irradiating, and
    venting the room temperature to 120° C. sweep air, wherein the venting the room temperature to 120° C. sweep air includes venting to an on-the-tarmac adsorbent bed.

2. The method of claim 1, wherein the pellets are formed using a mold.

3. The method of claim 1, wherein the venting the room temperature to 120° C. sweep air includes venting to the atmosphere.

* * * * *